United States Patent [19]

Sulc et al.

[11] Patent Number: 4,834,753
[45] Date of Patent: May 30, 1989

[54] SYNTHETIC INTRAOCULAR LENS SWELLABLE IN SWELLING AGENT AND A METHOD FOR PREPARATION THEREOF

[75] Inventors: Jiří Sulc; Zuzana Krcová, both of Praha, Czechoslovakia

[73] Assignee: Ceskoslovenska akademie ved, Czechoslovakia

[21] Appl. No.: 134,222

[22] Filed: Dec. 17, 1987

[30] Foreign Application Priority Data

Dec. 19, 1986 [CS] Czechoslovakia .................. 9596-86

[51] Int. Cl.$^4$ .............................................. A61F 2/16
[52] U.S. Cl. ........................................................ 623/6
[58] Field of Search ............................................ 623/6

[56] References Cited

U.S. PATENT DOCUMENTS 4,731,079  3/1988  Stoy ........................................ 623/6

*Primary Examiner*—Ronald L. Frinks
*Attorney, Agent, or Firm*—Leydig, Voit & Mayer

[57] ABSTRACT

The invention relates to a synthetic intraocular lens swellable in physiologic saline which is made from a polymer or a copolymer, at least one component of which is hydrophylic and the other one may be hydrophobic, crosslinked or non-crosslinked, whereas the content of swelling agent in it is below the equilibrium state whereby its glass-transition temperature $T_g$ is between $-5°$ C. and $45°$ C. The lens is deformed above $T_g$ into a form suitable for surgical insertion, cooled below $T_g$, and stored and surgically applied at the temperature below $T_g$, and then relaxed in eye by postswelling and heating. The lens may be incompletely swollen, instead in physiologic saline or water, in another physiologically harmless liquid, advantageously in glycerol.

8 Claims, No Drawings

SYNTHETIC INTRAOCULAR LENS SWELLABLE IN SWELLING AGENT AND A METHOD FOR PREPARATION THEREOF

The invention pertains to a synthetic intraocular lens swellable in a swelling agent such as physiologic saline, which is able to replace a natural lens of eye and is determined for introduction inside the eye, i.e. into its interior or posterior chamber or closely under cornea. These lenses are elastic and soft during their function in eye, advantageously in such a way that they are particularly soft at those places of their surface, by them the lens leans against the tissues of eye.

Such lenses are hitherto used for this purpose, which are in a definite shape and physical state before surgical introduction into eye. The lenses are either from hard polymers, as are polymers of methacrylic esters with lower aliphatic alcohols, for example, methyl methacrylate (MMA), or from soft hydrogels swollen to equilibrium in physiologic saline prior to introduction into eye. A relatively long incision is necessary in both these cases to slide the lens to its proper place. The hard lenses cannot be deformed at all at applicable temperature in order to facilitate the insertion and the common hydrogel lenses from lightly crosslinked polymers, e.g. polymer of 2-hydroxyethyl methacrylate (HEMA), have the deformation temporarily limited, if not excluded, for their elasticity and a tendency to break at not very sharp bending. In addition, the hard lenses increase the risk of wounding the sensitive tissues of eye at their introduction to place.

The invention ensues from a presumption, that it would be suitable if the intraocular lens can be maintained in a purposefully deformed state before and during operation, which would enable to reduce the incision to minimum, and if it then acquire a final shape in eye in the predetermined place. The purposeful deformation is, for example, coiling or compressing of the lens to a narrow rod, or at least its simple or multiple folding, to reduce the necessary length of incision at least to a half.

This purpose is attained according to the invention by modifying the glass-transition temperature $T_g$ of the lens material to the value being between the chosen temperature of environment (e.g. 20° C.) and temperature inside the eye (e.g. 35° C.) or higher. The subject of the invention is a synthetic intraocular lens swellable in a swelling agent such as a physiologic saline characterized by the content of swelling agent before its surgical introduction, which is chosen below the equilibrium state whereby its glass-transition temperature $T_g$ is between −5° C. and 45° C. The lens, which has the content of swelling agent decreased below the equilibrium state so that its $T_g$ is in the above given region, is deformed in the relaxed state into a shape suitable for surgical introduction, for example, by coiling from two sides, and cooled below $T_g$ to fix this deformation. After surgical insertion, which is considerably facilitated by the deformation, the lens relaxes in eye by post-swelling and, at the same time, is heated to the temperature of eye, thus obtaining the desired final shape.

The intraocular lens according to the invention may be already before deformation incompletely swelled in a non-aqueous physiologically inert liquid which is well soluble in water, for example, in glycerol or dimethylsulfoxide.

The material of lens may be crosslinked either covalently or non-covalently, or it may be non-crosslinked, provided that the used polymer or copolymer is sufficiently stable. A suitable value of $T_g$ may be easily attained by using a copolymer, at least one component of which forms a hydrophilic polymer and at least one other component forms a hydrophilic polymer, whereas the hydrophobic monomer component is usually used in a smaller amount than the hydrophilic component.

It is obvious that the choice of the limits of temperature region, where is the glass-transition temperature $T_g$, depends on the expected temperature of environment. In tropics or in summer, the deformed lenses should be stored in a suitable cooling equipment to prevent from an undesirable relaxation before application, Similarly, the deformed lens at temperature below $T_g$ must be protected from water vapor, which may be easily realized by storing in a suitable impermeable wrapping, e.g. from polyolefin or other foil which is not easily permeable for moisture. Another suitable wrapper is a sealed glass ampule The lens can be placed there in the dry, suitably deformed and sterile state, a calculated or previously determined amount of swelling agent may be added to it, which is not sufficient for the equilibrium swelling, and the ampule is sealed.

The hitherto most frequent material from a lightly crosslinked poly(2-hydroxyethyl methacrylate) can be used in the preparation of intraocular lenses according to the invention. However, it is also possible to add before polymerization a smaller amount of a suitable hydrophobic monomer (i.e. the monomer forming hydrophobic polymers), as are esters of methacrylic or acrylic acid with lower aliphatic alcohols, styrene, and the like. Any suitable method may be used for molding of the intraocular lens according to the invention, for example, rotation casting with parallel polymerization or copolymerization and/or crosslinking, or turning from a xerogel, or pressing, or injection molding, and others.

The non-crosslinked lenses can be additionally crosslinked, for example, by irradiation or by the additional introduction of a crosslinking agent and heating in the presence or absence of a suitable polymerization initiator. For shaping, e.g. by injection molding, also solutions of the considered polymer in a suitable solvent soluble in water may be used, which solvent is then removed by washing. The deformed lens relaxes after surgical insertion into eye soon, e.g. within several seconds to several hours, by post-swelling and its $T_g$ is correspondingly lowered at the parallel heating to eye temperature. The lens aquires the original shape, elasticity and softness by relaxation.

It is also purposeful to make softer those parts of lens, especially the parts of its circumference, which lean against the living tissues of eye in the final position, by known procedures. This may be attained by the additional local partial hydrolysis in alkaline or acid medium, neutralization and washing.

In addition to physiological saline or water, any other inert, harmless and water miscible liquid may be used for swelling to a non-equilibrium state before deformation, usually together with water or physiologic saline. Such liquid is, for example, glycerol or dimethylsulfoxide, monoesters and diesters of glycerol with a suitable organic acid, e.g. acetic acid, and the like. These additives reliably prevent from the contingent damage of lens with ice crystals during cooling and storage below 0° C.

Such deformation is advantageously chosen which enables, at a considerably reduction of size, above all width, an easy relaxation and achievement of the original shape. Internal stress occurs during deformation and cooling below $T_g$ in the deformed state, which is fixed by cooling. This stress can be developed either by a transverse deformation, for example, by coiling from two sides towards the central line, folding to three parts along two parallel lines, and pressing, or also by a longitudinal deformation, i.e. by a simultaneous or subsequent sretching of the coiled or folded lens in the longitudinal direction. In all cases, the deformation is carried out at temperature above $T_g$ or the incompletely swollen lens, which is cooled below $T_g$ in the deformed state and stored in this state until surgical application. The relaxation occurs then inside the eye spontaneously.

Although the usual lightly crosslinked polymer of 2-hydroxyethyl methacrylate, which $T_g$ was adapted to the same value by lowering the content of swelling agent, for example, of physiologic saline, to 10–20% (the equilibrium swelling approaches to 40% of water or a little less if physiologic saline is used), is quite suitable material for the intraocular lenses according to the invention, also various copolymers may be used, advantageously such copolymers, which have a higher equilibrium content of swelling agent, for example, 60% or more. Comonomers which are completely soluble in water are suitable for this purpose, for example, N-vinylpyrrolidine or methacrylamide, but the strength in a completely swollen is substantially lower with them. This disadvantage can be overcome by copolymerization with a lower amount of less hydrophilic or even hydrophobic monomer, as are some methyl, propyl or butyl esters of methacrylic or acrylic acid, styrene, acrylonitrile or methacrylonitrile, and others. N-substituted methacrylamides or acrylamides may be used as the hydrophilic component, whereas one or both substituents advantageously contain hydrophilic groups, for example, ether and/or hydroxyl groups. The content of swelling agent before deformation is adapted, of course, to the composition of copolymer in such a way, that the $T_g$ value is attained generally in the region $-5°$ C. to 45° C., advantageously between about 10° C. and 35° C. The upper limit may be the higher, the deeper below the equilibrium state is the content of swelling agent. Then $T_g$ is decreased very substantially by post-swelling to the equilibrium content of swelling agent and the relaxation is fast and efficient. It is obvious, that only the storage of the deformed lens below the glass-transition temperature and relaxation occuring in eye by post-swelling are decisive. The value to which the content of swelling agent has to be decreased in order to achieve the said aim may be easily ascertained by a simple experiment for any composition of the lens material.

The invention is illustrated in detail by the following examples of performance.

EXAMPLE 1

An intraocular lens made by polymer cast molding in a rotating mold from a mixture containing 50 wt. parts of glycerol, 49 wt. parts of 2-hydroxyethyl methacrylate (HEMA), 0.3 wt. parts of ethylene glycol dimethacrylate, and 0.7 wt. parts of isopropyl peroxocarbonate was washed in water, pressed to a glass base, and freed of an excess of water down to the content of 12 wt. % by heating to 35° C. (the equilibrium swelling was 39 wt. %). The lens was soft and pliable at this temperature and water content and was coiled from two sides towards the central line, stretched by about 40% of its length, and cooled to 15° C. in this state. After sterilization with gaseous oxirane, it was stored in a glass ampule and carefully sealed to be not heated above 20° C. After surgical insertion, which required only a short incision without sewing, the eye was allowed to rest for about 2 hours. After this period of time, the lens completely relaxed and assumed the original and final shape.

EXAMPLE 2

The monomer mixture containing 15 wt. parts of methyl methacrylate, 20 wt. parts of N-vinylpyrrolidone, 64 wt. parts of N-bis(hydroxyethyl)methacrylamide, and 1 wt. part of benzoin was charged into a transparent tube from silicone rubber and polymerized by irradiation with UV light. The resulting hard rod was cut to blocks from which intraocular lenses were made by turning. The amount of physiologic saline corresponding to 50% of the equilibrium swelling at 35° C. (the equilibrium swelling was 55 wt. %) was added to each lens placed in a glass ampule and the ampule with the content was sterilized at 120° C. for 20 minutes. The lens was then removed, deformed at temperature 38°–45° C., cooled to 20° C., sterilized with oxirane, and welded into a wrapping from 0.5 mm thick polyethylene foil. The lens was then stored in a cooling box at 8° C.

EXAMPLE 3

An intraocular lens manufactured by bulk polymerization cast molding from 2-hydroxyethyl methacrylate (HEMA), containing 0.3 wt. parts of ethylene glycol dimethacrylate, with 0.1 wt. parts of azobis(isobutyronitrile) (ABIN). The lens was machined and polished and placed in a glass ampule into which 20 wt. % of physiologic saline was added related to the weight of dry lens. The ampule was then sealed and sterilized in an autoclave. Before implantation, the lens was removed under sterile conditions from the ampule, heated in a special sterile equipment, deformed into a rod with diameter 2 mm, and cooled. It was inserted in this state through a 3-mm incision into the eye chamber when it reassumed its original shape within 10 seconds. A complete equilibrium swelling occurred after 10 minutes.

EXAMPLE 4

An intraocular lens manufactured in a mold by polymerization of 80 wt. % of 2-hydroxyethyl methacrylate (containing 0.3 wt. parts of ethylene glycol dimethacrylate and 0.1 wt. parts of azobis(isobutyronitrile)) and 20 wt. % of physiologic saline was removed from the mold and sealed in a glass ampule. Afterwards the intraocular lens was handled as described in Example 3.

We claim:

1. Synthetic intraocular lens swellable in swelling agent such as physiologic saline, wherein the content of swelling agent in the said lens is before surgical insertion below the equilibrium state whereby its glass-transition temperature is between $-5°$ C. and 45° C.

2. The synthetic intraocular lens according to claim 1, wherein the said lens is deformed at the temperature above its glass-transition into a form suitable for surgical insertion and cooled in this deformed state.

3. The synthetic intraocular lens according to claim 1, wherein the said lens is incompletely swollen with a nonaqueous physiologically inert liquid which is well soluble in water.

4. The synthetic intraocular lens according to claim 1, wherein the said lens is comprised of a copolymer, at least one component of which is hydrophilic in the polymerized state and at least one other component is hydrophobic in the polymerized state.

5. The synthetic intraocular lens according to claim 2, wherein said lens is comprised of a copolymer, at least one component of which is hydrophilic in the polymerized state and at least one other component which is hydrophobic in the polymerized state.

6. The synthetic intraocular lens according to claim 3, wherein said lens is comprised of a copolymer, at least one component of which is hydrophilic in the polymerized state and at least one other component which is hydrophobic in the polymerized state.

7. The synthetic intraocular lens according to claim 3 wherein said non-aqueous physiologically inert liquid which is soluble in water is preferably glycerol or dimethylsulfoxide.

8. Method of preparation of an intraocular lens which is swellable in a swelling agent such as physiologic saline or an inert liquid soluble in water wherein the content of swelling agent in said lens is below the equilibrium state before the surgical introduction of the lens into the eye comprising the steps of:
settling the content of the swelling agent in the lens to the level corresponding to the glass-transition temperature between −5° C. and 45° C.,
deforming the lens at the temperature above its glass transition temperature into a form suitable for surgical insertion, and
cooling the deformed lens to the temperature below the glass-transition temperature.

* * * * *